(12) United States Patent
Moreliere et al.

(10) Patent No.: US 9,975,842 B2
(45) Date of Patent: May 22, 2018

(54) METHOD FOR PRODUCING ALKYL (METH)ACRYLATES

(71) Applicant: Arkema France, Colombes (FR)

(72) Inventors: Anne Moreliere, Longeville-les-St-Avold (FR); Gilles Frimour, Dalstein (FR); Jean-Michel Paul, Metz (FR); Stephane Denis, Leyviller (FR)

(73) Assignee: ARKEMA FRANCE, Colombes (FR)

( * ) Notice: Subject to any disclaimer, the term of this patent is extended or adjusted under 35 U.S.C. 154(b) by 0 days. days.

(21) Appl. No.: 15/329,910

(22) PCT Filed: Jun. 22, 2015

(86) PCT No.: PCT/FR2015/051648
§ 371 (c)(1),
(2) Date: Jan. 27, 2017

(87) PCT Pub. No.: WO2016/016528
PCT Pub. Date: Feb. 4, 2016

(65) Prior Publication Data
US 2017/0267624 A1 Sep. 21, 2017

(30) Foreign Application Priority Data

Jul. 28, 2014 (FR) .................... 14 57262

(51) Int. Cl.
*C07C 67/48* (2006.01)
*C07C 67/08* (2006.01)
*C07C 67/54* (2006.01)

(52) U.S. Cl.
CPC .............. *C07C 67/08* (2013.01); *C07C 67/54* (2013.01)

(58) Field of Classification Search
CPC ......... C07C 67/08; C07C 67/54; C07C 69/54; Y02P 20/582
See application file for complete search history.

(56) References Cited

U.S. PATENT DOCUMENTS

| | | | | |
|---|---|---|---|---|
| 4,748,268 A | * | 5/1988 | Pietsch | C07C 67/08 560/205 |
| 6,492,546 B2 | | 12/2002 | Paul et al. | |
| 6,603,036 B2 | * | 8/2003 | Bessalem | C07C 67/08 560/205 |
| 7,943,094 B2 | * | 5/2011 | DeBruin | B01D 3/14 422/129 |
| 2002/0133041 A1 | * | 9/2002 | Paul | C07C 67/08 560/205 |
| 2004/0267045 A1 | * | 12/2004 | Yada | C07C 51/09 560/205 |
| 2015/0299093 A1 | * | 10/2015 | Riondel | C07C 67/08 560/214 |

FOREIGN PATENT DOCUMENTS

| | | |
|---|---|---|
| EP | 1219587 A1 | 7/2002 |
| FR | 2739850 A1 | 4/1997 |
| WO | WO2013064775 * | 5/2013 |

OTHER PUBLICATIONS

International Search Report and Written Opinion for International Application No. PCT/FR2015/051648, dated Oct. 2, 2015, 7 pages.

* cited by examiner

*Primary Examiner* — Yevgeny Valenrod
*Assistant Examiner* — Blaine G Doletski
(74) *Attorney, Agent, or Firm* — RatnerPrestia

(57) ABSTRACT

The present invention relates to a method for producing a $C_4$-$C_{10}$ alkyl (meth)acrylate, by direct esterification of (meth)acrylic acid by the corresponding alcohol, the reaction water being removed in the form of an azeotrope with the esterification alcohol from a distillation column mounted over the esterification reactor comprising a cationic resin as a catalyst. Said method is characterized in that the molar ratio of alcohol to acid at the inlet of the reactor is between 1.4 and 3, and in that the crude reaction mixture circulates in a recirculation loop joining the reactor and the water removal column, at a recirculation rate of between 6 and 25, expressed by the mass ratio between the flow fed into the loop and the flow sent to a purification treatment.

19 Claims, 4 Drawing Sheets

METHOD FOR PRODUCING ALKYL (METH)ACRYLATES

CROSS-REFERENCE TO RELATED APPLICATIONS

This is the national phase of International Application No. PCT/FR2015/051648, filed 22 Jun. 2015, which claims priority to French Application No. 1457262, filed 28 Jul. 2014. The disclosure of each of these applications is incorporated herein by reference in its entirety for all purposes.

FIELD OF TECHNOLOGY

The present invention relates to the production of alkyl (meth)acrylates by direct esterification of (meth)acrylic acid by the corresponding alcohol, said reaction being catalyzed by a cationic resin.

It relates more particularly to an improved method for producing $C_4$-$C_{10}$ alkyl (meth)acrylates, in particular 2-ethylhexyl acrylate, employing novel reaction conditions leading to simplification of the method and an increased rate of production of a product complying with the standards with respect to purity.

PRIOR ART AND THE TECHNICAL PROBLEM

The problems that arise during production of $C_4$-$C_{10}$ alkyl (meth)acrylates by direct esterification of (meth)acrylic acid in the presence of a cationic resin as catalyst are most often linked to the complexity of the purification steps required after the reaction step to obtain a product of high purity, generally to the detriment of process productivity.

In order to simplify the downstream purification operations, it was proposed in the method for producing unsaturated carboxylate described in document EP 1219587 in the applicant's name, to carry out the esterification reaction by ascending passage of the mixture of the reactants through a bed of a cationic resin, in a recirculating loop that is connected to a stirred tank in which the reactants are mixed together and from which the water of reaction is removed in the form of an azeotrope with the esterifying alcohol. The esterification reaction is carried out in the presence of a slight excess of alcohol, in particular with an overall acid/alcohol molar ratio between 0.6 and 1. According to one embodiment, a partial reaction upstream of the stirred tank is carried out by directing the mixture of reactants in ascending mode through a second bed of the cationic resin as catalyst.

Although this method leads to high degrees of conversion and to high selectivities, it seemed to the applicant that the complexity of the reaction zone and of its operation made the method difficult to implement and did not allow the desired purity to be obtained for the finished product.

In the method for producing methacrylic esters by direct esterification catalyzed by sulfuric acid, described in document U.S. Pat. No. 4,748,268, the reaction mixture at reactor outlet is fractionated continuously in a distillation column, into tops rich in the ester produced, and a bottoms stream containing the unreacted reactants, water, nonvolatile byproducts, the catalyst and a small amount of ester. This bottoms stream is partly returned to the reactor, thus constituting a recirculating loop in the installation.

After much research, the applicant found that it is possible to produce (meth)acrylic esters of high purity by direct esterification in a simplified reaction zone, using an excess of alcohol for the esterification reaction and recycling a high proportion of the reaction mixture in a recirculating loop only comprising the esterification reactor and a distillation column that removes the water produced in the form of an azeotrope with the esterifying alcohol. Surprisingly, these operating conditions make it possible to optimize the yield of the reaction, with efficient removal of the water produced by the reaction, thus minimizing the secondary reactions responsible for the formation of impurities and heavy byproducts, and therefore for a drop in process productivity.

The present invention therefore relates to an improved method for producing alkyl (meth)acrylates that is simple to implement, with a high yield and little generation of heavy byproducts, which simplifies the downstream purification operations. Moreover, the purified product only contains slight traces of impurities associated with the acid and the alcohol employed.

SUMMARY OF THE INVENTION

The present invention relates to a method for producing a $C_4$-$C_{10}$ alkyl (meth)acrylate by direct esterification of (meth)acrylic acid by the corresponding alcohol, the water of reaction being removed in the form of an azeotrope with the esterifying alcohol from a distillation column positioned above the esterification reactor comprising a cationic resin as catalyst, characterized in that the alcohol/acid molar ratio at reactor inlet is between 1.4 and 3, and in that the crude reaction mixture circulates in a recirculating loop linking together the reactor and the column for removing the water, at a recirculation rate ranging from 6 to 25, expressed as the weight ratio of the stream directed into the loop to the stream sent to a purification treatment.

The method of the invention further comprises a purification treatment of the crude reaction mixture leaving the recirculating loop comprising at least the steps:

(i) submitting the crude reaction mixture to distillation in a topping column to obtain:
   at the top, a stream consisting essentially of the unreacted reactants;
   at the bottom, a stream comprising the required ester, impurities associated with the acid and the alcohol, and heavy byproducts;

(ii) directing the bottom stream from the topping column to a rectification column for separating:
   at the top, the purified ester that is required;
   at the bottom, a stream containing impurities associated with the acid and the alcohol and heavy byproducts, which is concentrated on a film evaporator or distilled in a tailing column in order to recycle the light compounds present to the rectification column, and remove the final residue of heavy byproducts.

According to one embodiment of the invention, the operating conditions of the topping column are adjusted to entrain, at least partly, the light impurities associated with the acid or with the alcohol.

According to one embodiment of the invention, the bottom stream from the topping column is submitted to washing with an aqueous stream before it is sent to the rectification column in step (ii).

According to one embodiment of the invention, the topping step (i) is preceded by a step of distillation of the crude reaction mixture in a tailing column for separating part of the heavy byproducts.

DETAILED ACCOUNT OF THE INVENTION

The invention will now be described in more detail in the following nonlimiting description.

In the present description, the terms "between" or "ranging from" denote the inclusive range.

Figure 1:
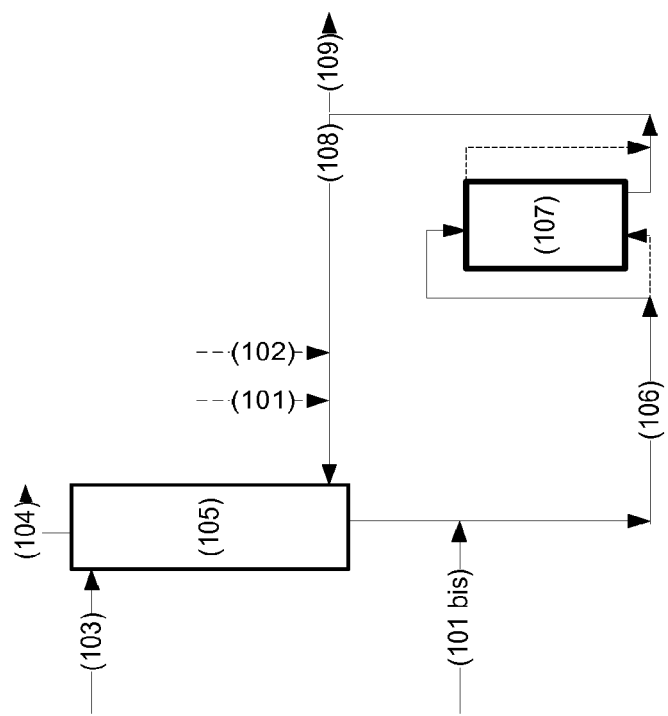
FIG. 1 is a schematic representation of the reaction section for carrying out the method according to the invention.

Referring to FIG. 1, generally the esterification reaction is carried out in a reactor (107) surmounted by a distillation column (105) for extracting the water generated by the reaction. The water of reaction is removed as it is formed in the form of an azeotrope with the esterifying alcohol in stream (104), in order to shift the esterification equilibrium.

The reactor may be a fixed-bed reactor or a suspended-bed reactor.

The assembly shown in FIG. 1 forms a recirculating loop in which the crude reaction mixture makes a certain number of passages through the reactor before being sent to a purification section. The assembly thus constitutes a stirred loop reactor with water removal. It is not necessary to include a stirred tank to ensure mixing of the reactants, said mixing being carried out directly in line owing to the presence of the recirculating loop.

The reactor may have descending or ascending feed, preferably descending. The (meth)acrylic acid may be fed to the inlet of the column (stream 101) or to the bottom of the column (stream 101 bis). The alcohol (103) is fed directly to the distillation column. A recycling stream (102) containing unreacted alcohol and acid from the purification section may also be introduced into the recirculating loop, notably at the inlet of the distillation column.

The distillation column, generally packed, is equipped with a top condenser, a decanter, receiver and trap (not shown in the figure), for decanting the vapors condensed at the top and separating an organic phase comprising alcohol and traces of ester, which is recycled to the column, and an aqueous phase, which is removed. The column generally operates at a pressure in the range from 50 to 70 mmHg.

According to the invention, the esterification reaction is carried out in conditions with excess of alcohol; in particular, the alcohol/acid molar ratio at reactor inlet is between 1.4 and 3, preferably between 1.8 and 2.3. The alcohol/acid molar ratio refers to the contents of alcohol and acid in the various streams feeding the esterification reactor (stream of pure reactants, recycled stream and recirculated stream). In-line analysis of stream (106) after removal of the water of reaction entering the reactor makes it possible to adjust the feed streams of pure reactants to obtain the desired ratio.

The reactor comprises a cationic resin as esterification catalyst, preferably a strong cationic resin, for example a strong sulfonated cationic resin of the styrene/divinyl benzene type with sulfonic groups. As examples of resins, we may mention those marketed under the names DIAION® PK208 or PK216 by the company Mitsubishi, or those marketed under the name LEWATIT® K2620 or K2621 by the company Lanxess, or those marketed under the name AMBERLYST® A15, A16 or A46 by the company Rohm & Haas.

The reaction temperature is generally between 70° and 100° C., preferably between 75° C. and 95° C. The presence of the recirculating loop makes it possible to use a lower temperature with a constant production rate.

The reaction is generally carried out in the presence of at least one polymerization inhibitor selected from phenothiazine, hydroquinone (HQ), and derivatives thereof such as hydroquinone methyl ether (HQME), 2,6-di-tert-butyl-4-methylphenol (BHT), 2,4-dimethyl-6-tert.-butylphenol (Topanol A), salts of thiocarbamic or dithiocarbamic acid, N-oxyl compounds, such as 4-hydroxy-2,2,6,6-tetramethyl piperidinoxyl (4-OH Tempo), compounds with nitroso groups, such as N-nitrosophenyl hydroxylamine and ammonium salts thereof, quinones such as benzoquinone, and amino compounds such as derivatives of paraphenylenediamine, at contents in the reaction mixture that may be between 50 ppm and 5000 ppm, optionally in the presence of depleted air, but generally at contents between 150 ppm and 1000 ppm. The polymerization inhibitors may be added in various places, with the introduction of the reactants or at the top of the distillation column.

According to the invention, the crude reaction mixture from the reaction is sent to the recirculating loop, at a recirculation rate ranging from 6 to 25, this rate being expressed by the weight ratio of the stream directed into the loop to the stream sent to the purification treatment, in particular by the weight ratio between the flow rate of recirculating crude reaction mixture (108) and the flow rate of crude reaction mixture leaving the loop (109). Preferably, the recirculation rate is between 10 and 20, more preferably between 10 and 15. In these conditions, the total residence time of the crude reaction mixture in contact with the catalytic resin, expressed by the ratio of the volume of resin to the total volume flow rate of reactant feed is between 2 hours and 6 hours, advantageously between 2.5 hours and 5 hours.

The method according to the invention applies to the synthesis of $C_4$-$C_{10}$ alkyl (meth)acrylates, the esterifying alcohol being a primary or secondary aliphatic alcohol, comprising a linear or branched alkyl chain having from 4 to 10 carbon atoms. As examples of alcohols, we may mention butanol, 2-ethylhexanol, n-octanol, 2-octanol, n-decanol and 2-propylheptanol.

Preferably, the alcohol is 2-ethylhexanol or 2-octanol.

Preferably, acrylic acid is used.

The method according to the invention makes it possible to optimize removal of the water of reaction from the stream entering the reactor, which advantageously has the effect of limiting the formation of acidic impurities associated with the presence of (meth)acrylic acid.

In fact the problem that arises when using acrylic acid is formation of β-hydroxypropionic acid (called "HPA" hereinafter), and of β-acryloxypropionic acid (called AA "dimer" hereinafter).

HPA probably forms from the AA dimer in the presence of water and in contact with the resin. Its formation depends on the reaction operating conditions, the nature of the cationic resin used, and the amount of water present.

Regarding the AA dimers, their formation is detrimental to the amount of heavy byproducts to be incinerated, and consequently to the productivity.

The same types of impurities may also form in the case of methacrylic acid, in particular β-hydroxymethylpropionic acid and β-methacryloxypropionic acid.

The operating conditions of the invention minimize the formation of these impurities and make it possible to obtain, after the purification section, the required ester free from impurities associated with the acid, and complying with the standards with respect to purity for preparing polymers in most fields of application, notably pressure-sensitive adhesives (PSA).

Owing to the other secondary reactions that may lead to the formation of heavy byproducts, the esterifying alcohol and the (meth)acrylic acid that have net yet reacted add on to the double bond of the ester already formed (Michael addition) to form (methyl)propionic and (meth)acryloxypropionic derivatives whose boiling point is above the boiling points of (meth)acrylic acid, the esterifying alcohol and the ester formed.

These heavy byproducts pose a problem of loss of raw materials and a problem of separation and treatment for final removal.

It was observed, surprisingly, that the operating conditions of the method according to the invention lead to less formation of heavy byproducts, resulting in simplification of the purification section and improvement of the materials balance.

Figure 2:
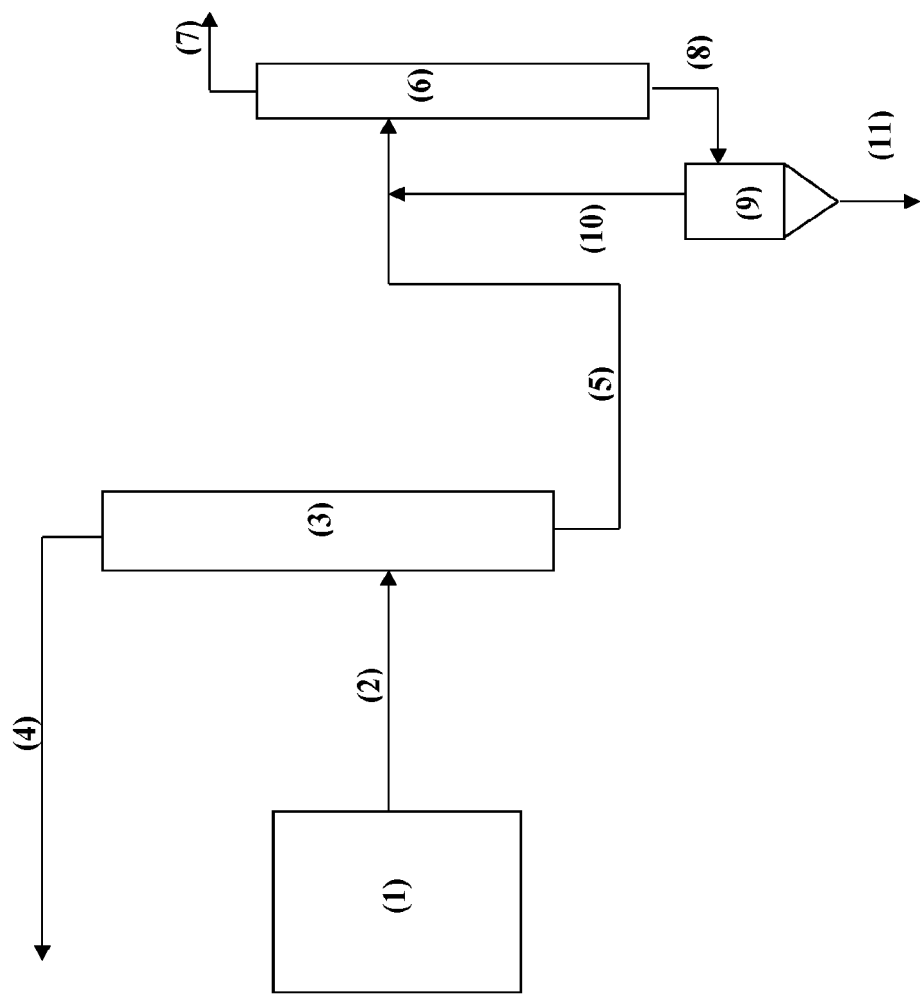
FIG. 2 is a schematic representation of the purification section of the method according to the invention.

After the reaction zone, the reaction mixture leaving the recirculating loop is submitted to a purification treatment, shown for example in FIG. 2, in which the recirculating loop is shown schematically at (1).

The crude reaction mixture (2) leaving the recirculating loop is sent to a topping column (3) which separates, at the top, a stream (4) essentially comprising the unreacted reactants, and at the bottom, a stream (5) mainly comprising the required ester with impurities associated with the acid and the alcohol and heavy byproducts. Column (3) is for example a plate column, of the perforated plate type, or a packed column. Stream (5) is sent to a rectification column (6) leading at the top to a stream (7) of purified ester, and at the bottom to a stream (8), which is concentrated in a film evaporator (9) or distilled in a topping column (not shown) in order to recycle the light compounds (10) present to the start of the purification section, such as traces of unreacted reactants, and remove the final residue (11) of heavy products.

Stream (4) essentially comprises the unreacted reactants, (meth)acrylic acid and esterifying alcohol, which are separated from the required ester on account of their lower boiling point. This stream (4), which can be utilized, is recycled to the reaction. In the case when impurities associated with the acid are formed in the reaction zone, it is possible to adapt the operating conditions of the topping column so as to entrain the HPA formed (in the case of acrylic acid) in the overhead stream recycled to the reaction. The HPA recycled to the reaction may react with the esterifying alcohol to give alkyl hydroxypropionate, which is easily removed with the fraction of heavy byproducts at the bottom of the rectification column. This embodiment of the invention also contributes to the production of a final product free from residual acidity.

According to one embodiment of the invention, the reaction mixture is washed with water after topping, before separating the impurities and the heavy byproducts in the rectification column.

Figure 3:
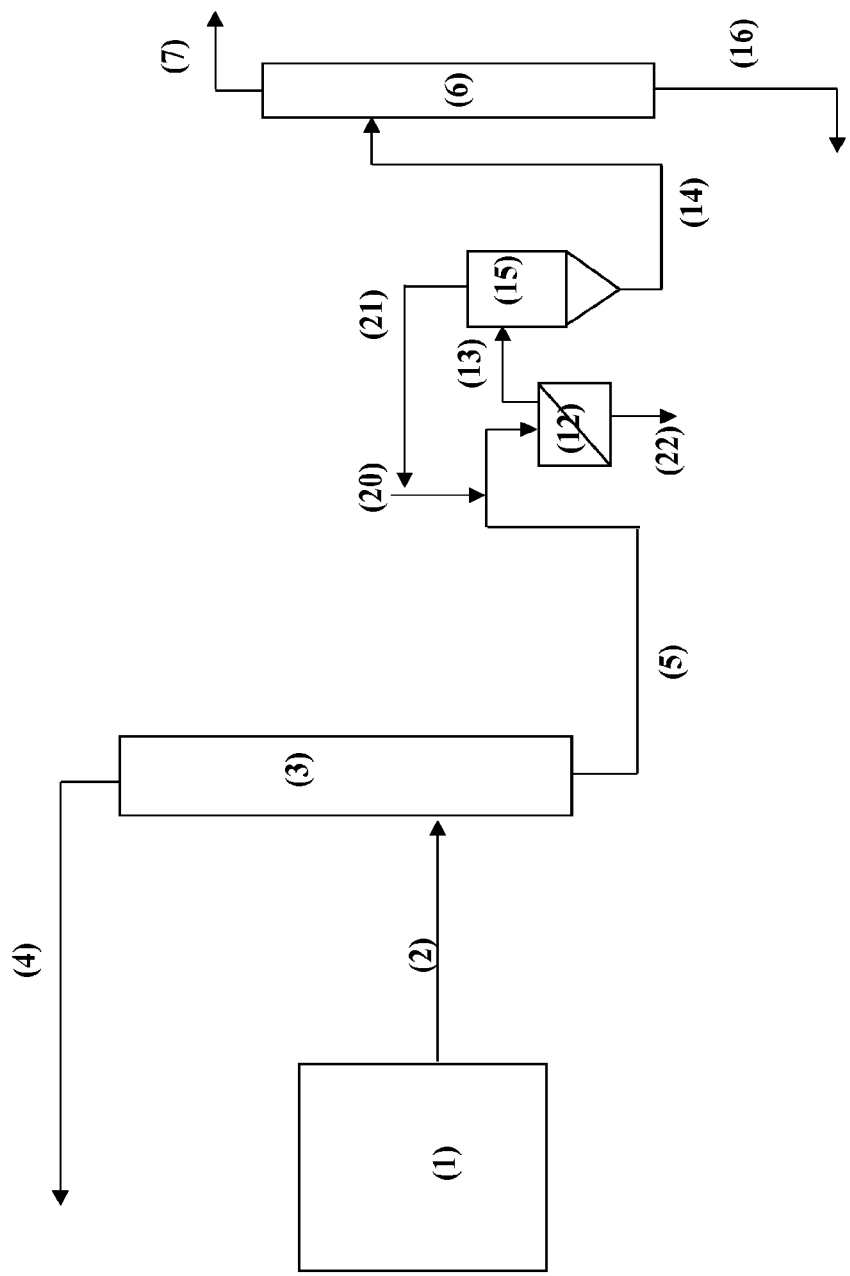
FIG. 3 illustrates one embodiment of the purification section of the method according to the invention, including a step of washing the topped stream.

According to this embodiment, illustrated in FIG. 3, the purification treatment of the reaction mixture leaving the recirculating loop comprises at least the steps:
(i) submitting the crude reaction mixture to distillation in a topping column to obtain:
at the top, a stream consisting essentially of the unreacted reactants;
at the bottom, a stream comprising the required ester, impurities associated with the acid and the alcohol, and heavy byproducts;
(i)a submitting the bottoms stream from the topping column to washing with an aqueous stream to obtain, after decanting,
an aqueous phase comprising all of the impurities associated with the (meth)acrylic acid, and
an organic phase comprising the required ester, heavy byproducts and traces of water and of (meth)acrylic acid;
(ii) submitting said organic phase, after removal of the water, to a rectification column for separating:
at the top, the purified required ester
at the bottom, a stream containing heavy byproducts, which is concentrated on a film evaporator or distilled in a tailing column in order to recycle the light compounds present to the rectification column, and remove the final residue of heavy byproducts.

Referring to FIG. 3, the bottoms stream (5) from the topping column (3) generally contains more than 90 wt % of ester, or even more than 94 wt % of ester, impurities associated with the acid and the alcohol, and heavy byproducts, as well as the polymerization inhibitors.

According to the invention, the water extraction step is carried out with an aqueous stream (20), which comprises pure water, or water from the reaction step, or a mixture of the two in all proportions.

The washing temperature is not critical; it is generally between 25° C. and 100° C., preferably between 50° C. and 70° C.

Of the order of 5 g to 10 g of water is used per 100 g of stream (5), in order to remove all the impurities associated with the acid, which would pose a risk of catalyzing the decomposition of the heavy compounds subsequently in the purification process. It is not necessary to use more water to remove all the acidic impurities.

Washing with 10% of water makes it possible, for example, to lower a content of HPA of the order of 120 ppm to less than 1 ppm and reduce the content of AA dimer by 15 to 20%.

The amount of washing water is preferably optimized in relation to the content of AA dimer present in stream (5).

The aqueous phase (22) contains the bulk of the impurities associated with the acid, and a small amount of acid.

The organic phase (13) decanted in the decanter (12) contains the ester and a minor fraction of heavy compounds and light compounds with residual water, of the order of 3500 ppm to 5000 ppm of water, which it is preferable to remove before submitting said phase to the final distillation.

The organic phase obtained after washing with water is therefore submitted to a step of removal of water, and the water recovered can be recycled to the washing step.

The water present in said organic phase (13) may be removed by distillation using a distillation column or using a thin film evaporator (15). In a preferred embodiment of the invention, a thin film evaporator of the Luwa type is used. The operating conditions, given only as a guide, are in this case a pressure of 150 mbar, a temperature at the top of the evaporator of 24° C., an oil temperature of 130° C., an evaporator top/bottom mass distribution of 10/90.

Passage through the evaporator (or distillation column) makes it possible to reduce the water content to more than 95% in stream (14) and generate an aqueous distillate (21), which may contain a small amount of ester, which is recycled, fully or partly, to the washing step.

The aqueous stream (20) used for washing is thus preferably a mixture of the aqueous stream (21) from the process, topped up with fresh water.

The water-free stream (14) is then sent to the last rectification column (6) of the pure ester. Column (6) is for example a plate column, of the perforated plate type, or a packed column. Because the bulk of the acid dimer was removed in the water washing step, the operating conditions of column (6) are facilitated and decomposition of the heavy compounds is minimized.

The product distilled at the top of column (6) is a purified ester no longer containing impurities such as HPA, and having a content of esterifying alcohol generally below 500 ppm and a content of acid dimer generally below 100 ppm.

Stream (16) at the bottom of column (6), rich in heavy compounds and possibly containing traces of ester, may be partially recycled or removed.

Figure 4:
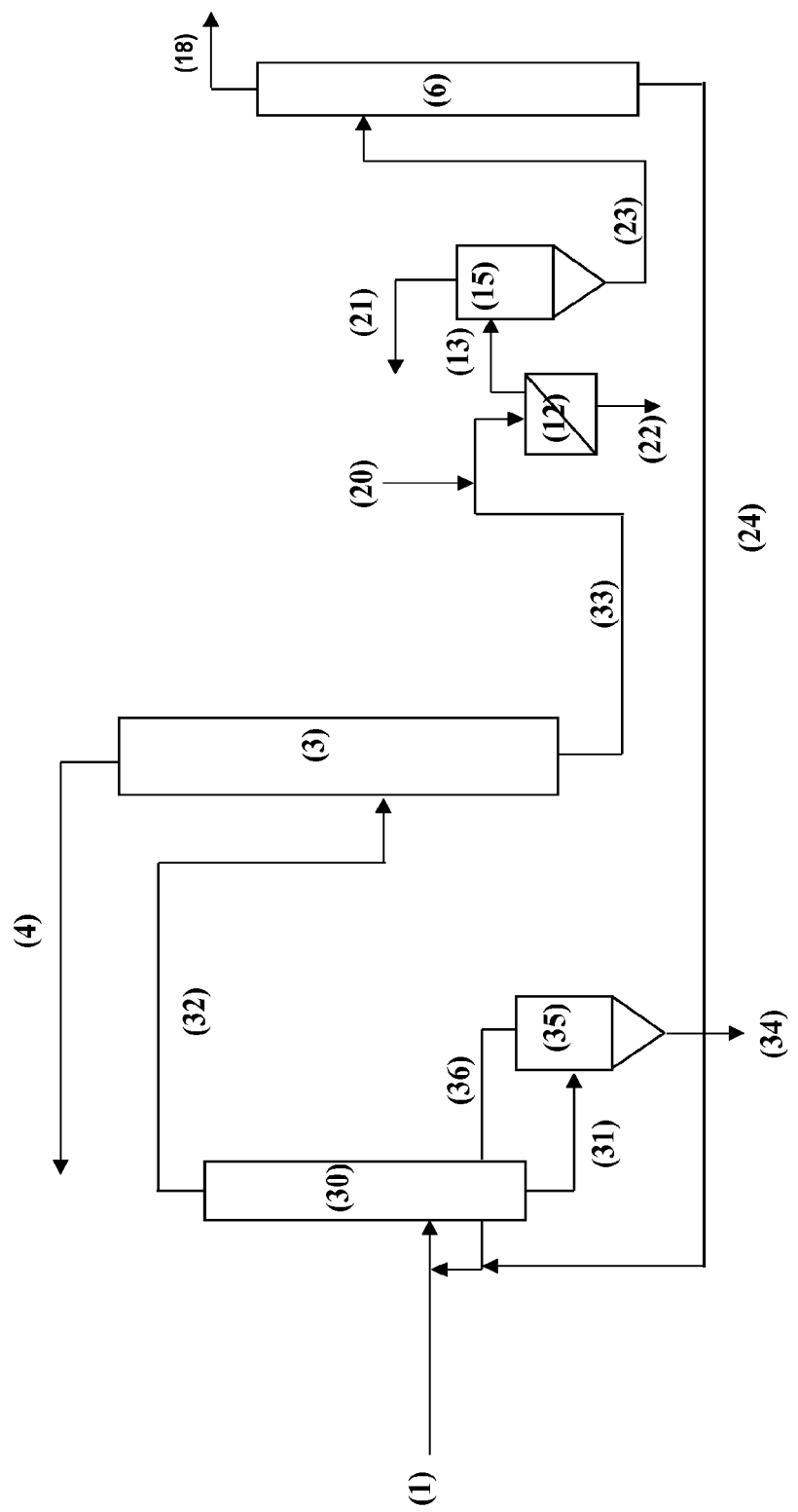
FIG. 4 illustrates one embodiment of the purification section of the method according to the invention, including a preliminary step of tailing the crude reaction mixture.

According to another embodiment of the invention illustrated in FIG. 4, the topping step (i) is preceded by a step of distillation of the reaction mixture in a tailing column for separating, at the bottom, a stream comprising the bulk of the acid dimer and heavy compounds, with traces of ester, and at the top, a stream comprising the ester, the unreacted reactants and impurities associated with the acid and traces of heavy compounds, said overhead stream then being submitted to the topping step (i).

According to this embodiment of the invention, the bottoms stream from the topping column in step (i), as well as the organic phase washed in step (i) a, contain impurities associated with the acid and heavy compounds in reduced amount, which makes it possible to reduce the amount of bottoms stream from the final distillation column and obtain a pure product without residual acidity and free from residual alcohol.

Referring to FIG. 4, the topping column (3) is preceded by a tailing column (30), of the plate column or packed column type.

The reaction mixture (1) is sent to a first distillation column (30) in order to separate the bulk of the acid dimer and heavy compounds (tailing) and submit a stream depleted of acid dimer and heavy compounds to the topping step.

The bottoms stream (31) from column (30) contains, besides the acid dimer and heavy compounds, traces of light compounds and ester.

This stream (31) is advantageously concentrated, for example on a film evaporator (35) allowing the light compounds with the ester to be recycled to the feed of column (30), and remove the heavy residues (34), for example by incineration.

The overhead stream (32) from column (30), from which the majority of the heavy compounds and almost all the acid dimers have been removed, is then sent to the topping column (3), giving an overhead stream (4) containing the light products with traces of ester. The bottoms stream (33) from the topping column (3) comprises more than 90 wt %, or even more than 94 wt % of ester, impurities associated with the acid and heavy compounds not separated in the tailing step, and traces of light compounds.

As in the embodiment described above, this stream (33) is treated with an aqueous stream (20) so as to remove impurities associated with the acid.

An amount of water of the order of 10% relative to the stream to be treated generally makes it possible to remove all of the impurities associated with the acid in the aqueous phase, and part of the acid dimer, the content of which is already reduced owing to the prior tailing step.

The decanted aqueous phase (22) containing the impurities associated with the acid is removed or recycled. The organic phase (13) is sent to the dryer (15), which may consist of a column or preferably a film evaporator.

The stream (21) containing water and ester is recycled, wholly or partly, for washing the stream (33), thus minimizing the content of fresh water (20) to be introduced into the washing circuit.

The dried stream (23) is sent to a final rectification column (6), from which the purified ester (18) leaves at the top. At the bottom, stream (24) containing ester and traces of alcohol is advantageously recycled to the feed of column (30).

According to this embodiment of the invention, an ester is obtained that is free from residual acidity and has an alcohol content generally below 200 ppm and a content of acid dimer generally below 5 ppm.

By employing a step of separation of the heavy compounds in the tailing column (30) upstream of separation of the light compounds in the topping column (3), a stream that is almost free from acid dimer and heavy compounds can be transported to the rest of the distillation train.

Absence of these impurities in the stream (23) feeding the rectification column (6) of the pure product can facilitate the operation of this, distillation column, reduce the reflux ratio and the heating power on the column, which leads to better productivity of the plant, reduced production of bottoms stream (24), and virtual absence of acid dimer in the pure ester. The content of residual alcohol in the pure ester is also reduced, owing to the virtual absence of heavy compounds and impurities associated with the acid in the feed of the final distillation column.

The following examples illustrate the present invention but without limiting its scope.

EXPERIMENTAL SECTION

In the examples, percentages are indicated by weight unless stated otherwise and the following abbreviations have been used:
AA: acrylic acid
A2EH: 2-ethylhexyl acrylate
2EH: 2-ethylhexanol
HPA: β-hydroxypropionic acid
Di-AA: AA dimers
PTZ: phenothiazine Example 1: Influence of the Alcohol/Acid Molar Ratio (MR)

The equipment used for synthesis of 2-ethylhexyl acrylate is a small synthesis pilot plant reproducing the operation of a stirred loop reactor with water removal, as shown in FIG. 1.

The reactor contains 340 ml (initial apparent volume) of cationic resin K2620 from Lanxess.

The reactor is fed with pure acrylic acid and 2-ethylhexanol. No recycled stream is introduced.

For each passage, the residence time of the reaction mixture on the resin, represented by the ratio of the volume of resin to the volume flow rate of the stream recirculated to the loop, is equal to 18 min. The total residence time, represented by the ratio of the volume of resin to the volume flow rate of the feed stream, is equal to 2.9 hours.

The distillation column is a laboratory column of the Vigreux type corresponding to about 6 theoretical stages, operating at a pressure of 80 mmHg, with a head temperature of 35° C. The water of reaction is removed in the form of an azeotrope with 2-ethylhexanol.

Two test series were carried out, the first series at a temperature of the bed of resin of 87° C., the second series at a temperature of 95° C.

The recirculation rate in the recirculating loop is equal to 7.9 or 8.

For each series, the feed rate of alcohol and acid was adjusted so that the molar ratio at reactor inlet was equal to 1.1 (or 1.2) and 2 (2.2).

For each test condition, 2 to 3 samples of reaction mixture were taken after at least 48 h of operation. The samples taken were analyzed by gas or liquid chromatography, to determine their composition by weight, and calculate the degrees of conversion and selectivities according to the following formulas:

Degree of conversion to acid,%=moles of acid converted/moles of acid in the feed×100

Selectivity of the ester relative to the acid,%=moles of ester formed/moles of acid converted×100

Selectivity of the ester relative to the alcohol,%=moles of ester formed/moles of alcohol converted×100

With the number of moles of acid converted calculated from the difference between the number of moles of acid in the feed and the number of moles of acid leaving the recirculating loop (in the aqueous phase at column top and in the outgoing crude reaction mixture);

With the number of moles of alcohol converted calculated from the difference between the number of moles of alcohol in the feed and the number of moles of alcohol leaving the recirculating loop (in the outgoing crude reaction mixture)

A balance is performed at the ends of the complete loop, quantifying the main byproducts.

The results are presented in Table 1.

TABLE 1

|  | Test 1 comparative | Test 2 | Test 3 comparative | Test 4 |
|---|---|---|---|---|
| Temperature, ° C. | 87 | 87 | 95 | 95 |
| Molar ratio 2EH/AA reactor inlet | 1.1 | 2 | 1.2 | 2.2 |
| Recirculation rate | 7.9 | 7.9 | 8 | 8 |
| Conversion AA, % | 66.0 | 71.5 | 73.8 | 79.3 |
| Selectivity ester/ AA converted, % | 98.7 | 99.9 | 97.5 | 99.8 |
| Selectivity ester/ 2EH converted, % | 100.2 | 100.1 | 97.9 | 97.4 |
| Balance, heavy byproducts/ester formed, g/kg | 43.1 | 34.3 | 60.0 | 46.6 |
| Di-AA/ester formed, g/kg | 1.3 | 0.6 | 2.0 | 0.7 |
| HPA/ester formed, g/kg | 0.31 | 0.19 | 0.48 | 0.31 |

These tests show that increasing the alcohol/acid molar ratio at reactor inlet makes it possible to improve the conversion of the acid (the concentration of AA at inlet being lower), but also the selectivity of the ester relative to the acid converted, for a selectivity of the ester relative to the alcohol that is roughly constant.

The alcohol/acid molar ratio at reactor inlet has an effect on the production of heavy byproducts, according to the invention, the amount of byproducts generated during the reaction decreases by more than 20%, which has a beneficial effect on purification of the ester and on the amount of materials removed. This effect is accentuated at the higher temperature.

The impurities associated with the acid are generated in a reduced amount in the conditions of the invention.

Example 2: Influence of the Alcohol/Acid Molar Ratio (MR)

This example illustrates the effect of the MR on an industrial production unit for 2-ethylhexyl acrylate at a scale of 90 tonnes/day.

The unit was operated with an alcohol/acid molar ratio at inlet of a catalyst bed ranging from 1.25 to 1.9 (3 productions P1, P2 and P3). The temperature was kept constant at 85° C., and the recirculation rate remained roughly identical.

The reactor is a fixed bed of 40 m$^3$ of a strong cationic resin of the macroporous type. It is fed in descending mode.

The results are presented in Table 2.

TABLE 2

|  | P1 comparative | P2 | P3 |
|---|---|---|---|
| Temperature, ° C. | 85 | 85 | 85 |
| MR | 1.25 | 1.6 | 1.9 |
| Recirculation rate | 10.5 | 11 | 12 |
| Overall degree of conversion of AA % | 69.1 | 69.4 | 71.3 |
| Selectivity ester/AA converted, % | 89.1 | 93.5 | 95.8 |
| Selectivity ester/2EH converted, % | 91.1 | 94.5 | 95.9 |
| Di-AA in the crude product, ppm | 325 | 240 | 149 |
| HPA in the crude product, ppm | 75 | 75 | 61 |
| Heavy byproducts in the crude product, ppm | 17900 | 12800 | 11600 |

Industrial production carried out in the MR conditions according to the invention gave a substantial improvement in selectivity of the ester relative to the acid and the alcohol and a crude product of 2-ethylhexyl acrylate containing only traces of impurities associated with the acid. Moreover, the method generated a smaller amount of heavy byproducts.

Example 3: Effect of Water on the Formation of Impurities Associated with the Acid and Heavy Byproducts This example has the aim of demonstrating the harmful effect of the presence of water in the reactor on the formation of HPA and of AA dimer, and on the total amount of heavy byproducts.

The equipment used is as in example 1 with the following operating conditions:
Resin A16 from DOW.
Reaction temperature: 88° C.
Feed rate of fresh AA: 39 g/h
Flow rate of the stream recirculating in the loop: 950 g/h
Recirculation rate: 8
Alcohol/acid molar ratio in the feed: 1.1
Alcohol/acid molar ratio entering the reactor: 1.2-1.3
Residence time in the reactor for one passage: 20.6 min
Total residence time in the reactor: 3.6 hours Test A was carried out using pure AA, and test B with a stream of AA with 1 wt % of water added.

The results in Table 3 show that the amount of impurities associated with the acid and heavy byproducts is greater in test B compared to test A.

TABLE 3

|  | Test A | Test B |
| --- | --- | --- |
| Acid feed | Pure AA | AA + 1% water |
| Conversion AA, % in one pass | 15.8 | 7.6 |
| Overall conversion of AA, % | 68.1 | 62.5 |
| Selectivity ester/AA converted, % | 40.2 | 42.4 |
| Selectivity ester/2EH converted, % | 72.4 | 74.3 |
| Balance of heavy byproducts/ester formed, g/kg | 41.9 | 54.5 |
| Di-AA/ester formed, g/kg | 1.2 | 2.3 |
| HPA/ester formed, g/kg | 0.34 | 0.79 |

Example 4: Influence of the Recirculation Rate

Two series of tests were carried out on an industrial unit, varying the recirculation rate in the recirculating loop.

In the same way, the conversion to acid, the selectivities for ester and the amount of heavy byproducts were determined from samples taken after at least 48 h of operation.

The results are presented in Table 4.

TABLE 4

|  | Test (a) | Test (b) |
| --- | --- | --- |
| Temperature, ° C. | 79 | 79 |
| Molar ratio 2EH/AA reactor inlet | 2.3 | 2.3 |
| Recirculation rate | 24 | 15 |
| Conversion AA, % | 75-80 | 68-72 |
| Balance of heavy byproducts/ester formed, kg/t | 22 | 26 |
| Di-AA/ester formed, kg/t | 0.001 | 0.001 |
| HPA/ester formed, kg/t | 0.02 | 0.11 |

The degree of conversion of the acrylic acid increases when the recirculation rate increases. The amount of heavy byproducts relative to the production of ester decreases when the recirculation rate increases.

The crude reaction mixture obtained in test (a) was submitted to a purification section as shown in FIG. 2. In particular, the topping column was controlled so as to separate most of the HPA column top and obtain an ester virtually free from impurities associated with the acid.

Table 5 presents the composition in wt % of the various streams: stream (2) at outlet of the reaction loop, stream (5) at the bottom of the topping column, stream (4) at the top of the topping column, and the stream of purified ester (7).

TABLE 5

| wt % | Stream (2) | Stream (5) | Stream (4) | Stream (7) |
| --- | --- | --- | --- | --- |
| A2EH | 61.2 | 97.4 | 26.1 | 99.79 |
| AA | 5.8 | <0.001 | 11.9 | 0.0007 |
| di-AA | 0.0068 | 0.032 | — | 0.0002 |
| HPA | 0.0029 | 0.0017 | 0.0042 | 0.0023 |
| Heavy products | 4.9 | 2.6 |  |  |
| Light compounds |  |  | 7.4 | — |

Example 5 (Referring to FIG. 3)

A crude reaction mixture (1) obtained by the method of the invention has the following composition by weight:
A2EH: 67.8%
2EH: 19.4%
AA: 7.7%
HPA: 119 ppm
AA dimer: 780 ppm
Heavy compounds: q.s. 100%

The crude reaction mixture is sent to a topping column (3) which separates, at the top, a stream (4) essentially comprising light compounds, notably the residual reactants AA and 2EH, water, octenes, a small amount of 2-ethylhexyl acetate and traces of A2EH, and, at the bottom, a stream (5) mainly comprising the required A2EH with impurities, including heavy byproducts.

Stream (4) is recycled to the reaction.

Stream (5) at the bottom of the topping column (3) has the following composition:
A2EH: 94.35%
2EH: 0.041%
AA: 17 ppm
HPA: 32 ppm
AA dimer: 1340 ppm Stream (5) is washed for 10 min at 70° C. with pure water (20), at a rate of 10 g of water per 100 g of stream (5), in a stirred vessel heated by circulation of oil in a double jacket (not shown), then the washed stream is decanted for 30 min at 70° C. in the decanter (12). The decanted organic phase (13) has the following composition by weight:
A2EH: 94.22%
2EH: 580 ppm
water: 3800 ppm
AA: 15 ppm
AA dimer: 1070 ppm
HPA: none
heavy compounds: q.s. 100%

It is observed that:
19% of the AA dimer passed into the decanted aqueous phase (22);
100% of the HPA is extracted in the aqueous phase;
10% of the total acidity (HPA+AA+AA dimer) passed into the aqueous phase.

The organic phase (13) is sent to a Luwa thin film evaporator (15), to remove the water from it, under the following conditions: T° oil 130° C.—P: 150 mbar.

The residual water content in the dried organic phase (14) is 100 ppm.

The composition by weight of stream (14) is as follows:
A2EH: 94.32%
2EH: 400 ppm
AA: 16 ppm
HPA: none
AA dimer: 1105 ppm
water: 100 ppm This stream (14) is distilled continuously on a packed column (6) having an efficiency of about 6 theoretical plates, with the conditions:

Top pressure: 39 mbar—T° top of column: 107° C.—T° bottom: 120° C.

Stream (7) of purified A2EH, distilled at the top of the column, has the following composition:
A2EH: 99.64%
2EH: 474 ppm
AA: 18 ppm
HPA: none
AA dimer: 60 ppm We obtain 2-ethylhexyl acrylate, free from HPA and depleted of residual 2-ethylhexanol.

Example 6

Example 5 is repeated, reusing the aqueous phase (22) 3 times in succession for washing the stream (5) (not shown in the figure).

Stream (5) is washed in the conditions of example 2 and then the decanted aqueous phase ($\varphi A_1$) is reused for washing the stream (5).

The decanted aqueous phase ($\varphi A_2$) is used for washing the stream (5) a third time. The decanted aqueous phase is designated ($\varphi A_3$).

|  | (22) | $\varphi A_1$ | $\varphi O_1$ | $\varphi A_2$ | $\varphi O_2$ | $\varphi A_3$ | $\varphi O_3$ |
|---|---|---|---|---|---|---|---|
| HPA, ppm | 30 | 287 | none | 563 | none | 832 | none |
| AA dimer, ppm | 1332 | 2003 | 1068 | 2357 | 1110 | 2386 | 1200 |
| AA, ppm | 142 | 28 | 30 | 32 | 33 | 37 | 34 |

This example shows that the washing water may be reused several times without loss of efficiency in removal of HPA, and thus reduce the consumption of clean water in the washing step.

Example 7 (Referring to FIG. 4)

A crude reaction product (1) has the following composition by weight:
A2EH: 66.26%
2EH: 20.64%
AA: 8.56%
HPA: 130 ppm
AA dimer: 684 ppm
Heavy compounds: q.s. 100%

The main heavy byproducts present in the crude (1) are:
2-ethylhexyl hydroxypropionate: 0.54%—2-ethylhexyl acryloxypropionate: 0.87%—2-ethylhexyl oxypropionate: 0.42%.

The total of the heavy byproducts present in the crude reaction product (1) represents 67.5 g/h.

The crude reaction product (1) is sent continuously to a Vigreux column (30) having a theoretical efficiency of about 5 theoretical plates at a flow rate of 3245 g/h for separating the bulk of the heavy byproducts (tailing). The conditions are as follows:
Column top pressure: 47 mbar;
Column top temperature: 100-108° C.;
Column bottom temperature: 115-120° C.
Flow rate of the overhead stream (32): 2953 g/h
Flow rate of the bottoms stream (31): 291.8 g/h The composition by weight of the overhead stream (32) of the tailing column (30) is:
A2EH: 65.46%
2EH: 22.92%
AA: 9.66%
HPA: 135 ppm
AA dimer: 14 ppm
heavy compounds: none The composition by weight of the bottoms stream (31) of the tailing column (30) is:
A2EH: 60.43%
2EH: 0.053%
AA: 11 ppm
AA dimer: 6340 ppm
Heavy compounds: 17.5% (i.e. 51.2 g/h)

Almost all the heavy compounds, as well as 97% of the AA dimer, are separated from the crude reaction product (1) and remain at the bottom of the tailing column (30).

The overhead stream (32) is free from heavy compounds and AA dimer, but contains nearly all the HPA.

The bottoms stream (31) is treated on a Luwa thin film evaporator (35), in the following conditions:
T° oil: 162° C.—pressure: 65 mbar—feed rate: 270 g/h.

86% of the heavy compounds remain at the bottom of the evaporator (35) and are removed in stream (34).

At the top of the evaporator (35), the outgoing stream (36) contains 70% of the A2EH, 86% of the 2EH and 39% of the AA dimer contained in stream (31); stream (36) is recycled to the tailing column (30).

The overhead stream (32) of the tailing column (30) is sent to the topping column (3).

The topping column (3) is of the same type as in the installations in FIGS. 2 and 3.

The operating conditions of column (3) are as follows:
Top pressure: 47 mbar
Top temperature: 105° C.—bottom temperature: 143-148° C.
Feed rate of stream (32): 2234 g/h
Flow rate of the overhead stream (4): 1203 g/h
Flow rate of the bottoms stream (33): 1030.9 g/h The composition by weight of the overhead stream (4) of the topping column (3) is:
A2EH: 40.44%
2EH: 40.06%
AA: 17.01%
HPA: 174 ppm
AA dimer: 26 ppm
Heavy compounds: none The overhead stream (4) from the topping column (3) is returned to the reaction.

The composition by weight of the bottoms stream (33) of the topping column (3) is:
A2EH: 99.49%
2EH: 0.03%
AA: <1 ppm
HPA: 24 ppm
AA dimer: 90 ppm
Heavy compounds: 0.03%

The bottoms stream (33) of the topping column (3) is washed with a stream of water (20) at 70° C. for 10 min (92.2 g of water for 922.2 g of stream (33)), then decanted at 70° C. for 30 min in the decanter (12).

915.7 g of decanted organic phase (13) and 94.7 g of aqueous phase (22) are recovered. The organic phase (13) is dried on a Luwa thin film evaporator (15), to remove the water from it, operating in the following conditions: T° oil: 100° C.—pressure: 38 mbar.

The composition by weight of the dried stream (23) is:
A2EH: 99.45%
2EH: 0.03%
AA<1 ppm
HPA: none
AA dimer: 77 ppm
water <100 ppm
Heavy compounds: 0.03%

Stream (23) is sent to the final distillation column (6), identical to that in examples 1 and 2, separating a stream (18) of pure A2EH at the top.

The operating conditions of column (6) are:
Top pressure: 39 mbar—T° top of column: 107° C.—T° bottom: 120° C.

The overhead stream (18) has the following composition:
A2EH: 99.72%
2EH: 195 ppm
AA: 8 ppm
HPA: none
AA dimer: <1 ppm
Heavy compounds: none We obtain a 2-ethylhexyl acrylate free from HPA and having a very low residual content of 2-ethylhexanol.

Stream (24) at the bottom of the distillation column of the pure product is returned to the feed of the tailing column (30).

The invention claimed is:

1. A method of producing a $C_4$-$C_{10}$ alkyl (meth)acrylate, comprising:
   (a) directly esterifying (meth)acrylic acid with an esterifying alcohol in an esterification reactor comprising a catalytically effective amount of a cationic resin to produce a crude reaction mixture comprising the $C_4$-$C_{10}$ alkyl (meth)acrylate and water of reaction,
      wherein the esterifying alcohol is a primary or secondary aliphatic alcohol having a linear or branched alkyl chain with 4 to 10 carbon atoms, and
      wherein the esterifying alcohol/(meth)acrylic acid molar ratio at reactor inlet is between 1.4 and 3;
   (b) circulating a first portion of the crude reaction mixture to a purification treatment;
   (c) circulating a second portion of the crude reaction mixture in a recirculating loop linking together the esterification reactor and a distillation column suitable for removing the water of reaction and positioned above the esterification reactor at a recirculation rate ranging from 6 to 25,
      wherein the recirculation rate is the weight ratio of the first portion of the crude reaction mixture circulated to the purification treatment to the second portion of the crude reaction mixture circulated to the recirculating loop; and
   (d) removing an azeotrope comprising the esterifying alcohol and water of reaction from the distillation column.

2. The method of claim 1, wherein the esterifying alcohol/(meth)acrylic acid molar ratio at reactor inlet is between 1.8 and 2.3.

3. The method of claim 1, wherein the recirculation rate is between 10 and 20.

4. The method of claim 1, wherein the recirculation rate is between 10 and 15.

5. The method of claim 1, wherein the (meth)acrylic acid is acrylic acid.

6. The method of claim 1, wherein the (meth)acrylic acid is methacrylic acid.

7. The method of claim 1, wherein the esterifying alcohol is selected from the group consisting of butanol, 2-ethylhexanol, n-octanol, 2-octanol, n-decanol and 2-propylheptanol.

8. The method of claim 1, wherein the esterifying alcohol is selected from the group consisting of 2-ethylhexanol and 2-octanol.

9. The method of claim 1, wherein the esterifying alcohol is 2-ethylhexanol.

10. The method of claim 1, wherein the crude reaction mixture has a total residence time in contact with the cationic resin of between 2 hours and 6 hours, wherein the total residence time is the ratio of the volume of cationic resin to the total volume flow rate of reactant feed.

11. The method of claim 1, wherein the crude reaction mixture has a total residence time in contact with the cationic resin of between 2.5 hours and 5 hours, wherein the total residence time is the ratio of the volume of cationic resin to the total volume flow rate of reactant feed.

12. The method of claim 1, further comprising:
   (e) purifying the $C_4$-$C_{10}$ alkyl (meth)acrylate.

13. The method of claim 12, wherein the purified $C_4$-$C_{10}$ alkyl (meth)acrylate contains less than 500 ppm of the esterifying alcohol and less than 100 ppm of acid dimer.

14. The method of claim 1, further comprising:
   (e) distilling the first portion of the crude reaction mixture in a topping column to produce:
      (i) a first stream comprising unreacted reactants at the top of the topping column; and
      (ii) a second stream comprising the $C_4$-$C_{10}$ alkyl (meth)acrylate, impurities associated with the (meth)acrylic acid and the esterifying alcohol, and heavy byproducts at the bottom of the topping column;
   (f) separating the second stream in a rectification column to produce:
      (i) a third stream comprising purified $C_4$-$C_{10}$ alkyl (meth)acrylate at the top of the rectification column; and
      (ii) a fourth stream comprising impurities associated with the (meth)acrylic acid and the esterifying alcohol, and heavy byproducts at the bottom of the rectification column; and
   (g) concentrating the fourth stream on a film evaporator or distilling the fourth stream in a tailing column, to recycle light compounds present to the rectification column and remove the heavy byproducts.

15. The method of claim 14, wherein impurities associated with the (meth)acrylic acid are at least partly entrained in the topping column.

16. The method of claim 14, further comprising, subsequent to (e) and prior to (f):
   (h) washing the second stream with an aqueous stream.

17. The method of claim 16, wherein 100 g of the second stream is washed with 5 to 10 g of water in (h).

18. The method of claim 16, further comprising, subsequent to (h):
   (j) decanting the washed second stream to produce:
      (i) an aqueous phase comprising impurities associated with the (meth)acrylic acid; and
      (ii) an organic phase comprising the $C_4$-$C_{10}$ alkyl (meth)acrylate, heavy byproducts, and traces of water and (meth)acrylic acid;
   (k) removing water from the organic phase; and
   (l) circulating the organic phase from (k) to (f).

19. The method of claim 14, further comprising, prior to (e):
   (m) distilling the first portion of the crude reaction mixture in a tailing column to separate a portion of heavy byproducts.

\* \* \* \* \*